United States Patent [19]

Garza et al.

[11] Patent Number: 5,205,175
[45] Date of Patent: Apr. 27, 1993

[54] MULTIPLE TRANSDUCER SELECTOR

[75] Inventors: José A. Q. Garza; George W. Gilman, both of Tempe; David J. Thomas, Mesa, all of Ariz.

[73] Assignee: Acoustic Imaging Technologies Corporation, Phoenix, Ariz.

[21] Appl. No.: 485,419

[22] Filed: Feb. 27, 1990

[51] Int. Cl.⁵ .................. G01N 29/24; A61B 10/00
[52] U.S. Cl. .................................. 73/628; 73/1 DV; 128/660.01; 128/660.07; 340/825.52; 340/825.57
[58] Field of Search ............ 340/825.52, 825.57, 340/825.04, 825.59; 73/628, 1 DV, 641; 128/660.07, 660.01

[56] References Cited

U.S. PATENT DOCUMENTS

| | | | |
|---|---|---|---|
| 3,629,856 | 12/1971 | Arai et al. | 340/825.04 |
| 4,448,076 | 5/1984 | van Heelsbergen | 73/628 |
| 4,568,931 | 2/1986 | Biolley et al. | 340/825.57 |
| 4,671,115 | 6/1987 | Ogawa et al. | 73/628 |
| 4,751,686 | 6/1988 | Uchino et al. | 73/606 |
| 4,811,740 | 3/1989 | Ikeda et al. | 128/660.01 |

OTHER PUBLICATIONS

"Multi-Port Dynamic Random Access Memory Controller", IBM Technical Disclosure Bulletin, vol. 34, No. 2, Jul. 1991 (pp. 495–498).

Primary Examiner—Hezron E. Williams
Assistant Examiner—Rose M. Finley
Attorney, Agent, or Firm—Christie, Parker & Hale

[57] ABSTRACT

An ultrasound imager supports several ultrasonic transducers simultaneously. The imager polls the transducer connection ports to determine which transducers are connected to which port and displays attributes of each transducer in conjunction with a port identification on the screen. The user selects which transducer is to be driven using a trackball or cursor arrow which directs an indicator to point to the selected transducer.

39 Claims, 3 Drawing Sheets

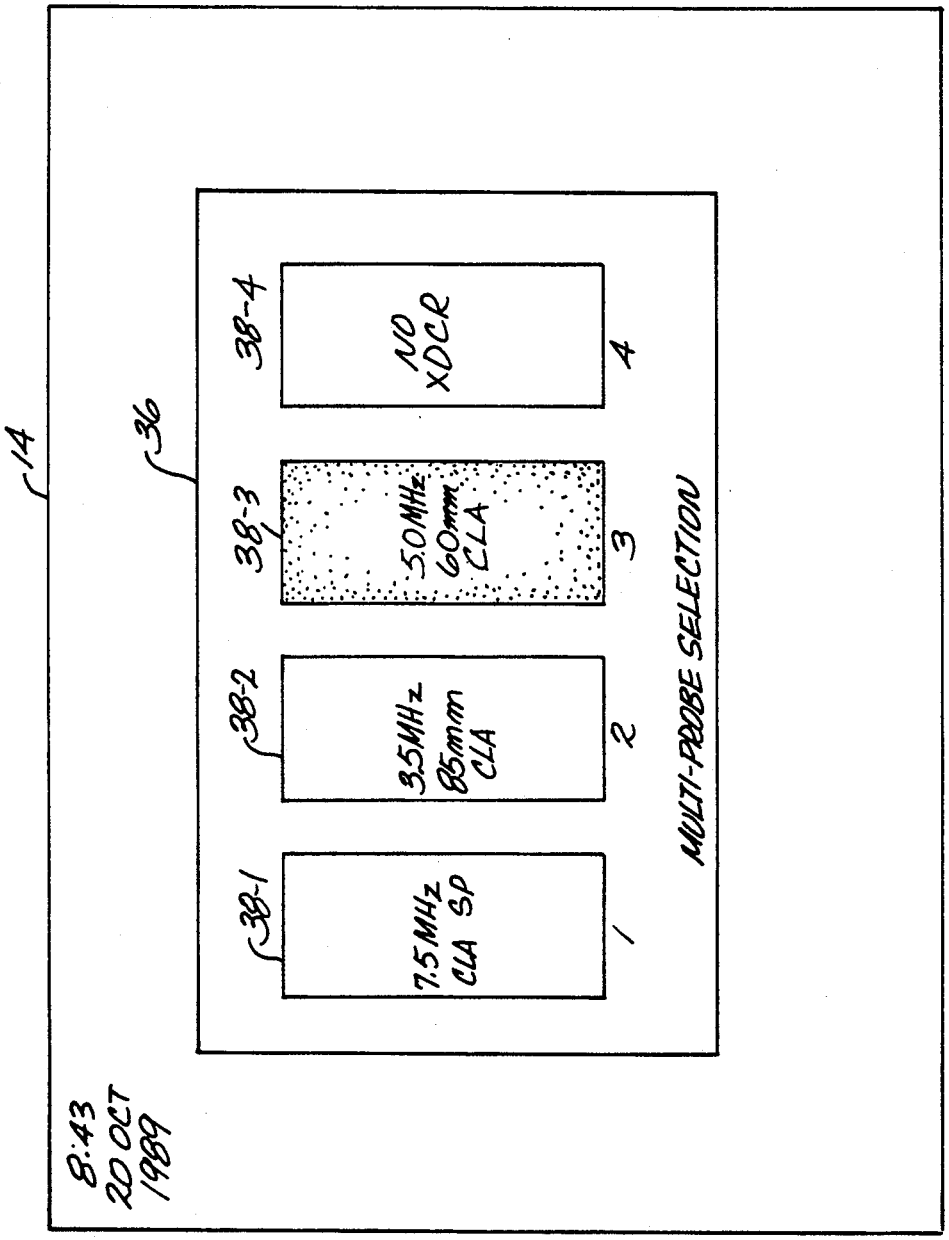

MULTIPLE TRANSDUCER SELECTOR

FIELD OF THE INVENTION

The present invention pertains to the field of ultrasound imaging and in particular to an ultrasonic diagnostic scanner capable of supporting multiple transducers.

BACKGROUND OF THE INVENTION

A variety of ultrasound imaging systems are well known in the art and are valuable for scanning and examining details below a surface. They are particularly useful in medical diagnosis because they allow real time imaging inside a patient's body without surgery and without penetration.

A modern ultrasound imaging system will usually support a variety of different transducing heads. The transducing heads are responsible for actually transmitting the ultrasound signals and receiving the echoes from within the body being examined. Different heads are better suited to different applications. The depth of penetration, resolution and contrast, for example, can vary greatly from one head type to another.

In a conventional ultrasound imaging system the head type is changed by unplugging one transducer head from a transducer port and then plugging a different head into the same port. In addition to being inconvenient, this arrangement causes interruptions in examinations which require that several different transducing heads be used.

SUMMARY OF THE INVENTION

The present invention avoids this problem by supplying a plurality of ports into which transducing heads may be inserted at the same time. The attributes of each transducer may be displayed simultaneously on a screen and the operator need only manipulate a keyboard to select which transducer is to be used.

In one embodiment, the invention is an ultrasonic imager with a plurality of ports, each capable of being connected to an ultrasonic transducer having a plurality of attributes. A control unit polls each port to determine the attributes of any connected transducers. The transducer attributes obtained from the poll are then shown on a display. The attributes may include the transmitting frequency of the transducer, the configuration array of the transducer head and model numbers. The control unit preferably polls each port to determine whether a transducer is connected to each port and displays this information as well.

The control unit drives the transducers connected to the ports and preferably includes a selector for determining which of the transducers is to be driven. The transducer selector has a trackball coupled to an indicator on the display so that, through rolling the trackball, a transducer is selected by positioning the indicator proximate a displayed set of attributes corresponding to the transducer to be selected. Alternatively, the selector has a keyboard coupled to an indicator on the display so that, through keystrokes, a transducer is selected by positioning the indicator proximate a displayed set of attributes corresponding to the selected transducer. The transducers are replaceable and the display is changeable upon replacing a transducer. In another embodiment, the invention comprises an ultrasonic imager with a plurality of ultrasonic transducers for transmitting and receiving ultrasonic signals and converting the received ultrasonic signals to electrical signals, each transducer being independently operable and having a set of attributes. A control unit coupled with the transducers drives the transducers and receives the electrical signals. The control unit has a display for simultaneously displaying at least some of the attributes of each transducer and a selector for determining which transducers are to be driven. The display also indicates which, if any, of the transducers are being driven.

BRIEF DESCRIPTION OF THE DRAWINGS

FIG. 3 is a sample screen display according to the present invention.

DETAILED DESCRIPTION

Figure 1:
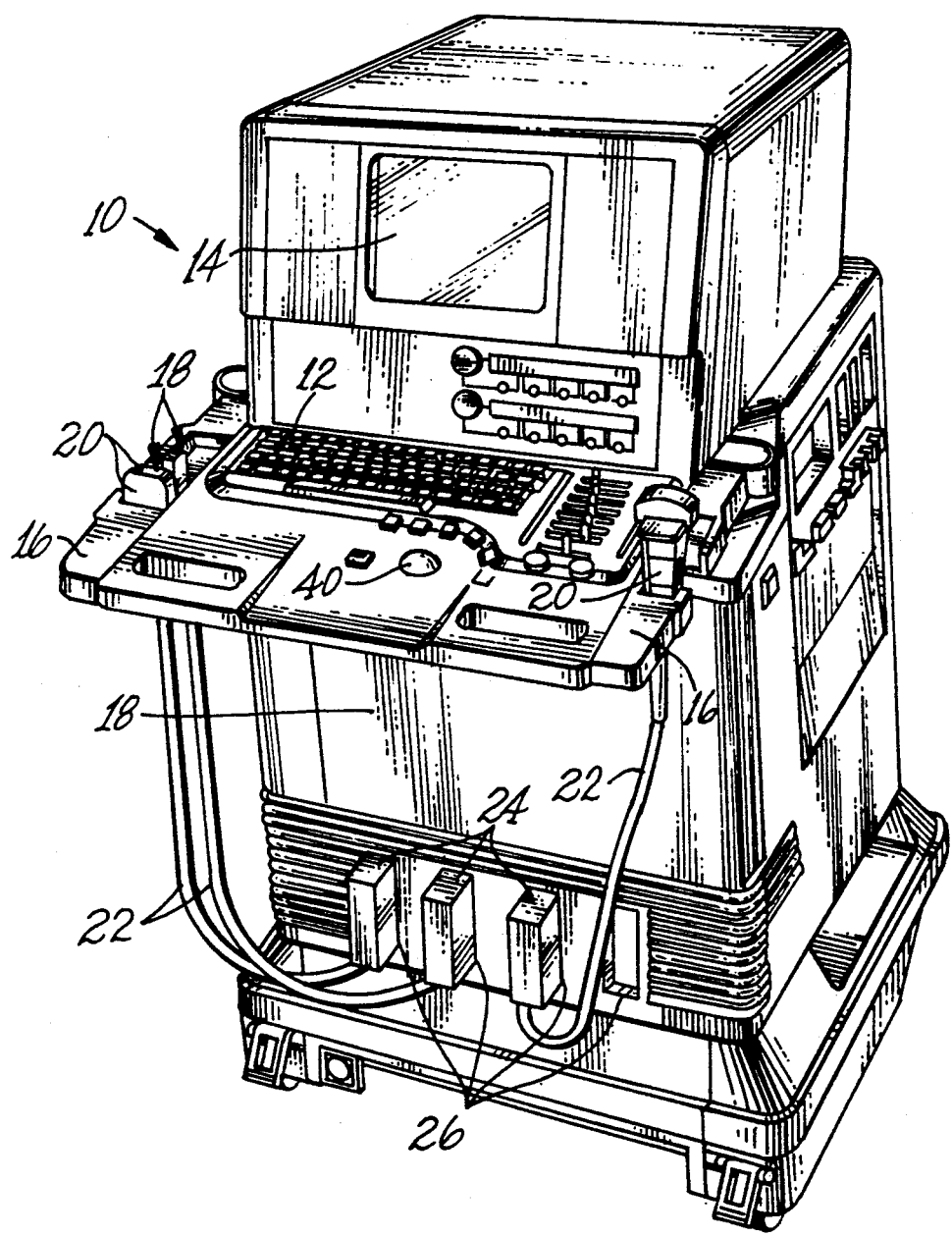
FIG. 1 is a perspective view of an ultrasonic imager according to the present invention.

FIG. 1 shows an acoustic imager 14 according to the present invention. The imager has a keyboard 12 for inputting data and a screen 14 for communicating with the operator and for displaying images received by the imager. On either side of the keyboard is a tray 16 for supporting transducers 18. The transducers have a head 20 connected by a cord 22 to an input block 24. The input block mates with ports 26 on a lower panel of the ultrasonic imager. While it is preferred that the imager can support as many as four different transducers, it is not necessary that four be installed at any one time. In FIG. 1 only three transducers are installed, one in port 1, one in port 2 and one in port 4.

The ultrasound imager is operated by, first, selecting a transducer for use, second, inputting this selection on the keyboard together with the desired performance parameters, for example, persistence, edge enhancement, compression, power output and image width, and, third, holding the transducer head over the body to be examined. The transducer emits high frequency sound waves which penetrate the surface of the body under examination and are reflected back to the transducer where they are detected. The detected sound waves are then converted into images. It is presently preferred that the apparatus described in Harrison, et al U.S. Pat. No. 5,140,558, issued on Aug. 18 1992, the disclosure of which is hereby incorporated fully by reference herein, be used to produce and process the images. However, imaging can also be done using well known methods and equipment. Techniques for holding a transducer head to obtain the desired image are also largely well known in the art. The imager 10 can support transducers with a variety of transducer array configurations including linear arrays and curved linear assay.

Figure 2:
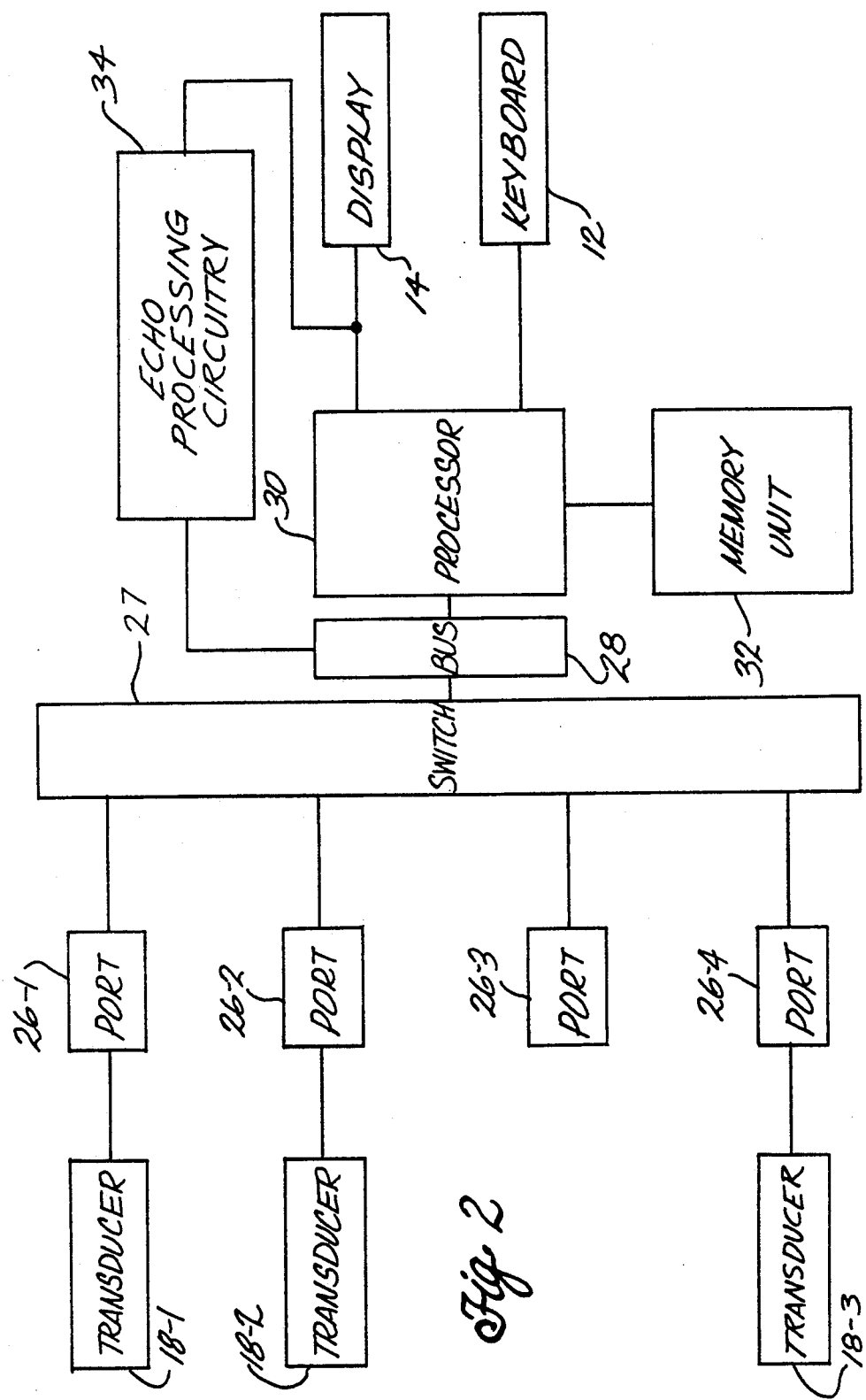
FIG. 2 is a block diagram of some working parts of the present invention.

FIG. 2 is a block diagram of some of the working parts of the ultrasound imager. As in FIG. 1, there are three transducers 18-1, 18-2 18-4 plugged into three of the four ports 26-1 to 26-4. These ports connect to a shared switching network 27 which connects to a shared bus 28 and then to a processor 30. The processor receives instructions from the keyboard 12 and transmits information to the display 14 where it can be read by the processor. The processor also has access to a memory unit 32. The bus, processor, display, keyboard and memory unit are all part of a control unit, which is responsible for driving the transducers and is housed in the main housing of the imager 10 shown in FIG. 1. The switching network 27 like the memory and display is controlled by the processor to the switch in addition to carrying signals between the processor and the ports. The switch has a set of switches or relays which control which of the ports is coupled to the processor.

FIG. 1 of U.S. Pat. No. 5,140,558 shows a block diagram of an ultrasound imaging system into which the invention can be incorporated. The disclosure of this application has been incorporated fully herein by reference. With reference to that figure, the processor 30 and memory unit 32 here are part of the main system processor 35, bus 27 herein are part of bus 14, keyboard 12 herein is part of control panel 39 and display 14 herein corresponds to the scan converter 36 and the video display terminal 38. In operation of the transducer selected in accordance with the invention, the echoes received by the selected transducer are coupled by the corresponding port, switch 27, and bus 28 to echo processing circuitry 34, where signals are formed to operate display 14. Preferably, the circuitry 34 is that disclosed in FIG. 1 of the referenced application. In terms of the invention, the signals generated by the processor 30 and the memory unit 32 to form the image of FIG. 3 herein are fed to the scan converter 36 and displayed on the screen of the video display terminal 38 of the referenced application.

When the operator wishes to begin an examination, he first must select a transducer to use. First, he keys a transducer selection start command into the keyboard. This instructs the processor to poll each of the ports 26-1 to 26-4 to determine if a transducer has been plugged into that port and, if so, what its attributes are. It is presently preferred that each transducer use multiple pin electric connectors to the ports. The polarity of three or four of the pins on each transducer input block 24 is hardwired to form an identification number. To poll each of the ports the processor operates the switch 27 to connect with each port one at a time. At each port it detects the identification number hardwired at the dedicated pins. Each identification number is then compared to a look-up table in the memory unit 32. The look-up table contains the attributes of the transducer as well as adjustable transducer operating parameters and instructions on how the transducer is to be driven. The memory unit 32 is preferably a hard disk drive or other rewriteable medium so that transducer identification numbers and transducer characteristics can be updated. After polling each of the ports and comparing the identification number at each port to values in the look-up table, the processor produces the window of FIG. 3 in the display.

In FIG. 3, the window 36 is preferably presented as an overlay to what is already being shown on the display and shows four separate boxes 38-1, 38-2, 38-3 and 38-4. Each box corresponds to one of the ports within the box. The attributes of the transducer installed into each port is displayed. The first box 38-1 displays three attributes of the transducer installed into port one, first, that it has an operating frequency of 7.5 megahertz (MHz), second, that it is a curved linear array (CLA), and third, that it is particularly suited to examining small parts (SP). The second box 38-2 shows that the transducer at that port has an operating frequency of 3.5 MHz, has an 85 millimeter head and also has a curved linear array (CLA). The third box 38-3 shows that the transducer at that port operates at 5.0 MHz and has a 60 mm CLA head. The fourth box shows "NO XDCR" meaning that no transducer has been installed into the fourth port. Any variety of different attributes can be chosen for display, for example, LF for long focus and PVLA for peripheral vascular linear array. Performance parameters as well as model numbers can be displayed in the box to assist the operator in choosing the appropriate transducer.

After the start command is received and the polling is completed, the processor presents the window shown in FIG. 3. The operator must then choose which transducer he will use. In FIG. 3, the third box is highlighted. This indicates that the third port having a 5.0 MHz, CLA transducer is selected. The indication associated with the third box can take any form; for example, cursors, underlining, flashing or color signals may be used. The selection of the third transducer can be changed in a variety of ways. The keyboard of FIG. includes a convenient trackball 40. The transducer selection is altered by rolling the trackball. Rolling the trackball to the right moves the highlighter to the right and rolling the trackball to the left moves the highlighter to the left. When the desired transducer is highlighted, a select button on the keyboard is pushed to confirm the selection. For example, starting with the screen in FIG. 3, if the operator wished to use the transducer plugged into the first port 7.5 MHz, he would roll the trackball to the left until the first box was highlighted. He would then push the select key, lift the transducer head out of its tray, and begin the examination.

Alternatively, selection commands can be entered using cursor arrow keys. Beginning with the display shown in FIG. 3, the operator could push a left cursor arrow twice to highlight the first box and then push the select key. Other well known keyboard manipulation techniques may be used. The above two methods are preferred for their speed and simplicity. After a transducer is selected, the imager drives that transducer conventionally or as described in application Ser. No. 07/415,484 until a new selection is made. After the transducer has been selected, the operator keys a data acquisition command into the keyboard and the echo processing circuitry 34 becomes operative as described in the referenced application.

The present invention makes it unnecessary to continuously remove and reinstall the desired transducer into a single port as required by most ultrasonic imaging machines. It also makes it unnecessary for the operator to remember the characteristics of two different transducers and which port each transducer has been plugged into as required by most multiple port machines. The key attributes of each transducer are displayed on the screen menu when the transducer selection is made. It is preferred that the present invention be integrated into an ultrasonic imager that allows the operator to select all of the operation parameters, for example depth setting, persistence, edge enhancement, compression, gray scale, power output and image width, using the keyboard based on displayed menus. Preferably the processor consults the memory immediately after a transducer port has been selected to obtain the adjustable operation parameters for the selected transducer. These are then displayed on the screen, and the user can adjust the parameters using the keyboard. The selected adjustments are displayed and, when all the adjustments are completed, the user enters a command causing the imager to start driving the selected transducer according to the selected operation parameter adjustments.

Because the processor itself polls the ports to determine the identity of the transducers installed in each port, it is unnecessary to key in the attributes of the transducers as they are installed or even to know the transducer attributes before they are installed. The user simply installs the transducers, selects the transducer to be used first, based on the attributes shown on the display, sets the parameters of its operation, and begins the examination. The other transducers may be removed and replaced even during an examination because the ports are all polled before each selection to determine which transducers are resident there at the time of selection. Using the hard wired identification pins the imager can also be adapted to poll the port being used periodically to confirm the identity of the transducer while it is being used. This allows the operator to switch transducers by unplugging the one being used and plugging a different transducer into the same port without returning to the keyboard.

Further details as to the precise operation of a preferred embodiment of the invention are contained in the source code listing in "C" language attached hereto as Appendix A. The code is suitable for use in the processor 30 of FIG. 2. While only a few embodiments have been discussed, the inventors in no way intend to limit their invention to these specific examples. A great variety of modifications and adaptations are possible within the spirit and scope of the present invention. For example, the screen displays may be significantly changed in appearance without detracting from the utility of the invention.

```
/* **************************************************************** *
 *      MODULE:  mprobe.c - Multi-probe select functions             *
 *                                                                   *
 *      All material herein Copyright (C) AITC, 1988                 *
 *      All rights reserved                                          *
 *                                                                   *
 * **************************************************************** */ include     <stdio.h>
include     <string.h>
#include     "defs.h"
#include     "options.h"
#include     "5200.h"
#include     "xdr_file.h"
#include     "globals.h"
#include     "ss_main.h"
#include     "mprobe.h"
#include     "dopbug.h"

#define      SGL_ULEFT       0xda
#define      SGL_LLEFT       0xc0
#define      SGL_URIGHT      0xbf
#define      SGL_LRIGHT      0xd9
#define      SGL_HORZ        0xc4
define      SGL_VERT        0xb3 define      MP_BORDER       1
define      MP_NUM_PROBES   4
#define      MP_HSPACE       2
#define      MP_VSPACE       2
#define      MPW_HEIGHT      10
#define      MPW_WIDTH       7
#define      MPW_TEXT_X      0
#define      MPW_TEXT_Y      4
#define      MP_HEIGHT       ( 2 * (MP_VSPACE+MP_BORDER) + MPW_HEIGHT )
#define      MP_THRESH       15
#define      MP_WIDTH        ( (MP_HSPACE+MPW_WIDTH+2*MP_BORDER) * MP_NUM_PROBES )

#define      MP_X1           6
#define      MP_Y1           ( USCR_YCMAX/2 - (MP_HEIGHT+2*MP_BORDER)/2 )
#define      MP_X2           (MP_X1 + MP_WIDTH)
#define      MP_Y2           (MP_Y1 + MP_HEIGHT)

#define      MPW0_X1         (MP_X1 + MP_HSPACE + MP_BORDER)
#define      MPW0_Y1         (MP_Y1 + MP_VSPACE + MP_BORDER)
#define      MPW0_X2         (MPW0_X1+MPW_WIDTH-1)
#define      MPW0_Y2         (MPW0_Y1+MPW_HEIGHT-1)

#define      MPW1_X1         (MPW0_X2 + MP_HSPACE + 3*MP_BORDER)
#define      MPW1_Y1         (MPW0_Y1)
#define      MPW1_X2         (MPW1_X1+MPW_WIDTH-1)
#define      MPW1_Y2         (MPW1_Y1+MPW_HEIGHT-1)

#define      MPW2_X1         (MPW1_X2 + MP_HSPACE + 3*MP_BORDER)
#define      MPW2_Y1         (MPW1_Y1)
```

```
#define     MPW2_X2     (MPW2_X1+MPW_WIDTH-1)
#define     MPW2_Y2     (MPW2_Y1+MPW_HEIGHT-1)

#define     MPW3_X1     (MPW2_X2 + MP_HSPACE + 3*MP_BORDER)
#define     MPW3_Y1     (MPW2_Y1)
#define     MPW3_X2     (MPW3_X1+MPW_WIDTH-1)
#define     MPW3_Y2     (MPW3_Y1+MPW_HEIGHT-1)

typedef struct {
   SHORT    x1 ;
   SHORT    y1 ;
   SHORT    x2 ;
   SHORT    y2 ;
   BOOL     bSlctd ;
   BOOL     bLoaded ;
   SHORT    nID ;
   CHAR     sFreq[MPW_WIDTH+1] ;
   CHAR     sDescr[MPW_WIDTH+1] ;
} MULTIPROBE_STRUCT ;

/** External data **/
extern struct DEBUGFLAGS  Debug ;

/** Local data **/
MULTIPROBE_STRUCT    tMProbe[MP_NUM_PROBES] = {
   {MPW0_X1, MPW0_Y1, MPW0_X2, MPW0_Y2,
     FALSE, FALSE, NO_XDCR, "NO XDCR", ""},
   {MPW1_X1, MPW1_Y1, MPW1_X2, MPW1_Y2,
     FALSE, FALSE, NO_XDCR, "NO XDCR", ""},
   {MPW2_X1, MPW2_Y1, MPW2_X2, MPW2_Y2,
     FALSE, FALSE, NO_XDCR, "NO XDCR", ""},
   {MPW3_X1, MPW3_Y1, MPW3_X2, MPW3_Y2,
     FALSE, FALSE, NO_XDCR, "NO XDCR", ""}
} ;
LOCAL SHORT   nSlctdPort = 0 ;
LOCAL SHORT   nCPort = 0 ;

/** Global data **/
BOOL  bMPScan = FALSE ;

/** Local function prototypes **/
LOCAL VOID DrawWindow(SHORT x1, SHORT y1, SHORT x2, SHORT y2) ;

/* *****************************************************************
 *   MPInit() - Multi-probe port select initialization
 *
 *   Revision History:
 *   -----------------
 *   06-Jun-1989    jaqg    Initial release
 *
 *   NOTES:
 *   ------
 *
 ***************************************************************** */
VOID
MPInit()
{
   SHORT    i ;

/** Allow main loop to scan port IDs **/
   bMPScan = TRUE ;

/** Disable multi-probe high voltage **/
   nCPort = MPGetPort() ;
```

```c
/** Open main window **/
open_window(MP_X1, MP_Y1, MP_X2, MP_Y2) ;
text_cursor(MP_Y2, MP_X1 + (MP_X2-MP_X1)/2 - 10) ;
uscr_printf("MULTI-PROBE SELECTION") ;
if (Debug.bDebugOn) {
    text_cursor(MP_Y2-1, MP_X1 + (MP_X2-MP_X1)/2 - 25/2) ;
    uscr_printf("PATENT SOON-TO-BE-PENDING") ;
}

/** Draw windows for each probe **/
for (i = 0; i < MP_NUM_PROBES; i++) {
    DrawWindow(tMProbe[i].x1, tMProbe[i].y1, tMProbe[i].x2, tMProbe[i].y2) ;
    strcpy(tMProbe[i].sFreq, "WAIT...") ;
    strcpy(tMProbe[i].sDescr, "") ;
    MPDisplay(i) ;
}

/** Scan IDs and set frequency, description strings **/
MPDisable() ;
for (i = 0; i < MP_NUM_PROBES; i++) {
    tMProbe[i].nID = MPScanID(i) ;
    MPLoad(i) ;
}
for (i = 0; i < MP_NUM_PROBES; i++) {
    /** Show frequency, description and hilight selected port **/
    tMProbe[i].bSlctd = (nCPort == i) ;
    if (tMProbe[i].bSlctd) {
        MPSetSlct(i) ;
    }
    MPDisplay(i) ;
} nSlctdPort = nCPort ;
}

/* ****************************************************************
 *      MPEntry() - Multi-probe port entry function
 *
 *      Revision History:
 *      -----------------
 *      06-Jun-1989    jaqg    Initial release
 *
 *      NOTES:
 *      ------
 *
 **************************************************************** */
VOID
MPEntry()
{
}

/* ****************************************************************
 *      MPCancel() - Multi-probe port cancel function
 *
 *      Revision History:
 *      -----------------
 *      06-Jun-1989    jaqg    Initial release
 *
 *      NOTES:
 *      ------
 *
 **************************************************************** */
VOID
MPCancel()
{
    MPSetPort(nCPort) ;
    MPEnable() ;
    close_all_windows() ;
    bMPScan = FALSE ;
}
```

```
/* ******************************************************************
 *    MPSelect() - Multi-probe port select
 *
 *    Revision History:
 *    -----------------
 *    06-Jun-1989    jaqg    Initial release
 *
 *    NOTES:
 *    ------
 *
 ****************************************************************** */
VOID
MPSelect()
{
   if (nSlctdPort != nCPort) {
      MPSetPort(nSlctdPort) ;
   } else {
      MPSetPort(nCPort) ;
   }
   MPEnable() ;
   close_all_windows() ;
   bMPScan = FALSE ;
}

/* ******************************************************************
 *    MPTb() - Multi-probe port trackball handler
 *
 *    Revision History:
 *    -----------------
 *    06-Jun-1989    jaqg    Initial release
 *
 *    NOTES:
 *    ------
 *
 ****************************************************************** */
VOID
MPTb(pxyTB)
   INT    *pxyTB ;
{
   LOCAL SHORT    x = 0 ;
   LOCAL SHORT    nNewPort = 0 ;

x += *pxyTB ;

if (abs(x) > MP_THRESH) {
      (x > 0) ? nNewPort++ : nNewPort-- ;
      Limit(&nNewPort, 0, MP_NUM_PROBES-1) ;
      if (nNewPort != nSlctdPort) {
         MPSetSlct(nSlctdPort = nNewPort) ;
      }
      x = 0 ;
   }
}

/* ******************************************************************
 *    MPDisplay() - Displays transducer frequency, description in window
 *
 *    Revision History:
 *    -----------------
 *    06-Jun-1989    jaqg    Initial release
 *
 *    NOTES:
 *    ------
 *
 ****************************************************************** */
VOID
```

```
MFDisplay(nPort)
    SHORT    nPort ;
{
    /** Show frequency, description **/
    text_cursor(tMProbe[nPort].y1 + MPW_TEXT_Y,
        tMProbe[nPort].x1 + MPW_TEXT_X) ;
    uscr_printf(tMProbe[nPort].sFreq) ;

text_cursor(tMProbe[nPort].y1 + MPW_TEXT_Y+1,
        tMProbe[nPort].x1 + MPW_TEXT_X) ;
    uscr_printf(tMProbe[nPort].sDescr) ;

/** Reverse video window if selected **/
    if (tMProbe[nPort].bSlctd) {
       set_char_attrib(REVERSE_CHAR,
           tMProbe[nPort].x1, tMProbe[nPort].y1,
           tMProbe[nPort].x2, tMProbe[nPort].y2) ;
    } else {
       reset_char_attrib(REVERSE_CHAR,
           tMProbe[nPort].x1, tMProbe[nPort].y1,
           tMProbe[nPort].x2, tMProbe[nPort].y2) ;
    }

/** Label **/
    text_cursor(tMProbe[nPort].y1-2, tMProbe[nPort].x1+3) ;
    uscr_printf("%1d", nPort+1) ;

if (Debug.bDebugOn) {
       /** ID # in hex **/
       text_cursor(tMProbe[nPort].y1 + MPW_TEXT_Y+2,
           tMProbe[nPort].x1 + MPW_TEXT_X + 3) ;
       uscr_printf("%02x", tMProbe[nPort].nID) ;
    }
}

/* ****************************************************************
 *    MFSetSlct() - Sets which port is selected
 *
 *    Revision History:
 *    ------------------
 *    06-Jun-1989    jaqg    Initial release
 *
 *    NOTES:
 *    ------
 *
 **************************************************************** */
VOID
MFSetSlct(nPort)
    SHORT    nPort ;
{
    LOCAL SHORT    nDispPort = 0 ;

if (nPort == nDispPort) {
       tMProbe[nPort].bSlctd = TRUE ;
       MFDisplay(nPort) ;
    } else {
       tMProbe[nDispPort].bSlctd = FALSE ;
       MFDisplay(nDispPort) ;
       nDispPort = nPort ;
       tMProbe[nDispPort].bSlctd = TRUE ;
       MFDisplay(nDispPort) ;
    }
}

/* ****************************************************************
 *    MPLoad() - Sets frequency and description strings for ID from files
 *
 *    Revision History:
 *    ------------------
 *    07-Jun-1989    jaqg    Initial release
```

```
*
*    NOTES:
*    ------
*
********************************************************************* */
VOID
MPLoad(nPort)
    SHORT    nPort ;
{
    CHAR      sXdrFile[13] ;
    XDCR_DATA tXdcr ;
    FILE      *fhXdcr ;
    SHORT     nRdErr ;

if (tMProbe[nPort].nID == NO_XDCR) {
        sprintf(&tMProbe[nPort].sFreq,  "NO XDCR") ;
        sprintf(&tMProbe[nPort].sDescr, "       ") ;
    } else {
        if (valid_xdcr_id(tMProbe[nPort].nID)) {
            /** LOAD **/
            sprintf(sXdrFile, "%02x.XDR", tMProbe[nPort].nID) ;

/** NOTE: This could be made more efficient by seeking to **/
            /**       and reading only the frequency and descriptions **/
            nRdErr = NULL ;
            if (fhXdcr = fopen(sXdrFile, "rb")) {
                if (nRdErr = fread(&tXdcr, sizeof(XDCR_DATA), 1, fhXdcr)) {
                    /** Load successful **/
                    strncpy(&tMProbe[nPort].sFreq[0], &tXdcr.freq[0], 3) ;
                    sprintf(&tMProbe[nPort].sFreq[3], " MHz") ;
                    strcpy(&tMProbe[nPort].sDescr, &tXdcr.displayed_description) ;
                }
            }
            if (!fhXdcr || !nRdErr) {
                /** Load or read failed **/
                sprintf(&tMProbe[nPort].sFreq,  "CANNOT ") ;
                sprintf(&tMProbe[nPort].sDescr, "LOAD %02x", tMProbe[nPort].nID) ;
            }
            fclose(fhXdcr) ;
        } else {
            sprintf(&tMProbe[nPort].sFreq,  "INVALID") ;
            sprintf(&tMProbe[nPort].sDescr, "ID = %02x", tMProbe[nPort].nID) ;
        }
    }
}

/* ********************************************************************
 *    MFScan() - Scans multi-probe IDs and updates display
 *
 *    Revision History:
 *    -----------------
 *    07-Jun-1989    jagg    Initial release
 *
 *    NOTES:
 *    ------
 *
 ********************************************************************* */
VOID
MFScan(nPort)
    SHORT    nPort ;
{
    BYTE    byID ;

/** Scan ID and redisplay if changed **/
    byID = MFScanID(nPort) ;
    if ((SHORT)byID != tMProbe[nPort].nID) {
        tMProbe[nPort].nID = (SHORT)byID ;
        MPLoad(nPort) ;
        MPDisplay(nPort) ;
    }
}
```

```
/* ****************************************************************
 *    MPInitialize() - Initializes multi-probe port
 *
 *    Revision History:
 *    -----------------
 *    26 Jul 1989    jaqq     Initial release
 *
 *    NOTES:
 *    ------
 *
 **************************************************************** */

VOID
MPInitialize()
{
   SHORT   i ;

/** Select first occupied port or 0 as default **/
   for (i = 0; i < 4; i++) {
      if (MPScanID(i) != NO_XDCR) {
         if (MPScanID(i) != NO_XDCR) {
            break ;
         }
      }
   }
   if (i > 3)
      i = 0 ;
   MPSetPort(i) ;
}

/* ****************************************************************
 *    DrawWindow() - Utility routine to draw window borders OUTSIDE x/y pr
 *
 *    Revision History:
 *    -----------------
 *    06-Jun-1989    jaqq     Initial release
 *
 *    NOTES:
 *    ------
 *
 **************************************************************** */

LOCAL VOID
   DrawWindow(x1, y1, x2, y2)
   SHORT    x1 ;
   SHORT    y1 ;
   SHORT    x2 ;
   SHORT    y2 ;
{
   SHORT    x, y ;

/** Top, bottom rows **/
   for (x = x1; x <= x2; x++) {
      text_cursor(y1-1, x) ;
      putc_uscr(SGL_HORZ) ;
      text_cursor(y2+1, x) ;
      putc_uscr(SGL_HORZ) ;
   }
   for (y = y1; y <= y2; y++) {
      text_cursor(y, x1-1) ;
      putc_uscr(SGL_VERT) ;
      text_cursor(y, x2+1) ;
      putc_uscr(SGL_VERT) ;
   }

/** Corners **/
   text_cursor(y1-1, x1-1) ;
   putc_uscr(SGL_ULEFT) ;
   text_cursor(y1-1, x2+1) ;
   putc_uscr(SGL_URIGHT) ;
   text_cursor(y2+1, x1-1) ;
```

```
   putc_uscr(SGL_LLEFT) ;
   text_cursor(y2+1, x2+1) ;
   putc_uscr(SGL_LRIGHT) ;
}

/* ************************************************************
 *    MFArrow() - Multi-probe select arrow key handler
 *
 *    Revision History:
 *    -----------------
 *    07 Aug 1989    jaqq    Initial release
 *
 *    NOTES:
 *    ------
 *    1) Translates arrow key to trackball movement
 *
 ************************************************************ */

VOID
MFArrow(nArrow)
   INT     nArrow ;
{
   INT     xyTB[2] ;

xyTB[0] = 0 ;
   xyTB[1] = 0 ;
   switch (nArrow) {
      case UP_ARROW:
         xyTB[1] = -14 ;
         break ;
      case DN_ARROW:
         xyTB[1] = 14 ;
         break ;
      case LF_ARROW:
         xyTB[0] = -16 ;
         break ;
      case RT_ARROW:
         xyTB[0] = 16 ;
         break ;
   }
   MFTb(&xyTB) ;
}

/*********************** ************************ :*******************
 *    MAIN - Root function for the AI5200 System Software.
 *
 *    Revision History:
 *    -----------------
 *        17 Aug 89   jaqq   Doppler (#DOP)
 *        12 Jul 89   jaqq   Port to Microsoft C 5.1 (MSC)
 *         2 jun 89   g2     In MAINTENANCE version, added call to xdcr_change()
 *                           when No_Xdcr_Change to support turnoff of tx ram when
 *                           the EID is attached. Also call set_tx_power() when
 *                           there is a change, to turn high voltage back on.
 *        14-aug-88   g2     Added call to xdcr_change_bus_on() every second.
 *         7-aug-88   g2     Revised for new menu engine.
 *        26-MAY-88   GTS    Baseline release.
 *
 *    NOTES:
 *    -----
 *    1) In passing digital pot info, it is assumed that knobs fill dp_array
 *       from [0] thru [NUM_KNOBS - 1] and trackballs from [NUM_KNOBS] on
 *       up.
 ************************************************************************/
int
main(argc, argv)
   int     argc ;            /* MSC */
   char    *argv[] ;         /* MSC */
{
   KBD_DATA key;
   int      key_action,
            kbd_raw,
            dp_array[NUM_DIGITAL_POTS];
```

```
/* ============================  MSC  ============================ */
    struct SREGS       s ;
    int                iHandle ;
    unsigned int       wDate ;
    unsigned int       wTime ;
    char               *sBuf[80] ;
    char               ssName[80] ;
    char               *ps ;
    static short int   nPort = 0 ;
    BOOL               bVersionOn = FALSE ;
    SHORT              nVersionCount = 0 ;
    INT                i;

BYTE  far * fpScRegs;           /* BKFIX */
    BYTE  bTemp;

if (argc > 1) {
        Debug.bDebugOn = TRUE ;
        beep() ;
    } else {
        Debug.bDebugOn = FALSE ;
    }

/**  Initialize Data Segment register  **/
    segread(&s) ;
    _dsval = s.ds ;

/**  #DOP Initialize pointers  **/
    BfInitPtr() ;
    MPInitPtr() ;
    dop_sc_regs(CLR, 0x2f, 01);      /* clearing bit 1 of 2f will prevent */
                                     /* the checkerboard pattern on */
                                     /* power up */

/**  Insure that Doppler flags indicate 2d  **/
    DopCtrl.nImageSize = SIZE_FULL ;
    DopCtrl.bDoppler = FALSE ;

/**  TEMPORARY debuggy type initialization  **/
    autoconfig() ;
    strcpy(ssName, argv[0]) ;
    _dos_open(ssName, O_RDONLY, &iHandle) ;
    _dos_getftime(iHandle, &wDate, &wTime) ;
    _dos_close(iHandle) ;
    for (ps = ssName; ps; ) {
        if (strchr(ps, '\\')) {
            ps = strchr(ps, '\\') ;
            ps++ ;
        } else {
            break ;
        }
    }
    strcpy(sExeFile, ps) ;

#ifdef ERROR_LOG
    /**  Open error logging file  **/
    if ( !(fhAILog = fopen("e:log", "w")) ) {
        _settextposition(24, 0) ;
        _outtext("  ERR - Cannot open <log>") ;
    }
endif ifdef PENCIL_IMAGE
    /  Initialize vector bank #2 for pencil  /
    dop_sc_regs(SET, 0x04, 0x80) ;
    enable_bus() ;
    enable_vector_load() ;
    DopSetVecBank2(SIZE_ONE_HALF) ;
    disable_vector_load() ;
    disable_bus() ;
    dop_sc_regs(CLR, 0x04, 0x80) ;
#endif
```

/* ============================ MSC ============================ */

```
    bMPScan = TRUE ;

initialize_5200();
    Initialize5200b() ;                              /* #DOP */ bMPScan = FALSE ;
    key_action = FALSE;

/*---------------------------------------------------------------
       ---- NO_COMPILE floating pt exception code
----------------------------------------------------------------*/
#ifdef NO_COMPILE
    WORD  far * fpTemp;              /* sig _i oebug */
                                     /* Trap floating point errors */
    _fpreset();                      /* ???? */ fpTemp = 0L;     /* NULL POINTER */
    sprintf(psMsg,"B4 Intr vec: %4x    %4x    ", *fpTemp, *fpTemp+1);
    aimsg(05,0);

if (signal(SIGABRT, FloatingPtError) == (int(*)()) -1) {
       sprintf(psMsg,"Unable to trap floating pt errors");
       aimsg(12,0);
/*** (VOID) signal(SIGFPE,SIG_DFL);   /* attempt to default fp handling */
    } else {
       sprintf(psMsg,"Trapped floating pt errors ");
       aimsg(12,0);
    }
    sprintf(psMsg,"addr fpe handler: %lx    ", &(FloatingPtError) );
    aimsg(13,0);
    sprintf(psMsg,"status87: %x    ", _status87() );
    aimsg(14,0);
/* sprintf(psMsg,"Second signal: %lx    ",(signal(SIGFPE, FloatingPtError) )  );
/* aimsg(15,0);
*/
    fpTemp = 0L;     /* NULL POINTER */
    sprintf(psMsg,"AF Intr vec: %4x    %4x    ", *fpTemp, *fpTemp+1);
    aimsg(6,0);
    getch();         /* < ====== BKFIX !!!   */
#endif
/*---------------------------------------------------------------
       END OF ---- NO_COMPILE floating pt exception code
----------------------------------------------------------------*/

/*---------------------------------------------------------------
                    System Main Loop
----------------------------------------------------------------*/ while(TRUE) {

/* If the footswitch or a key has been pressed, take the
          appropriate action */ if (scan_f_switch()) {
          key.class = FREEZE_KEY;
          key_action = TRUE;
       } ifdef PTEST
       if ((kbd_raw = cp_key()) == 0x10) { /* ^p */
          print_screen();
          print_ff();
       } else if (kbd_raw) {
          process_keystroke(kbd_raw, &key);
          key_action = TRUE;
       }
#else
       if (kbd_raw = cp_key()) {
          process_keystroke(kbd_raw, &key);
          key_action = TRUE;
```

```
            }
endif if (key_action) {
            if (Help_In_Progress)
                key.class = HELP_KEY;
            switch (key.class) {
                case DEL_KEY:
                case BACKSP_KEY:
                    if (CM.del_backsp_keys != NULLFPV)
                        (*CM.del_backsp_keys)();
                    break;
                case FREEZE_KEY:
                    process_key( &CM.freeze_key, 0, BEEP_IF_NULL);
                    break;
                case OTHER_NORMAL_KEY:
                    process_key( &CM.other_key, key.value, DONT_BEEP_IF_NULL);
                    break;
                case SOFTKEY:
                    process_key( &CM.sk[ key.value - 1], 0, BEEP_IF_NULL);
                    break;
                case UP_ARROW:
                case DN_ARROW:
                case RT_ARROW:
                case LF_ARROW:
                    if (CM.arrow_key.pexit_fn)
                        (*CM.arrow_key.pexit_fn)( key.class);
                    break;
                case HELP_KEY:
                    if (CM.help_key != NULLFPV)
                        (*CM.help_key)();
                    break;
                case OTHER_EXTENDED_KEY:
                    ;
            }
            key_action = FALSE;
        } if (!Help_In_Progress) {

/* If any of the digital pots (the soft knobs and the trackball)
               have been manipulated, update whatever they are now controlling */ if (scan_dpots(dp_array)) {
                vector_knob_data(dp_array);
                vector_trackball_data(&dp_array[NUM_KNOBS]);
            }

/* If any of the slidepots have been manipulated, update whatever
               they are now controlling */ if (CM.slidepots)
                (*CM.slidepots)();

/* If the frame rate has changed, display it */ show_frame_rate_display();
        }

/*------------------------------------------------------------------
            DEBUG code
------------------------------------------------------------------*/
#ifdef NO_COMPILE
        FP_SEG(fpScRegs) = 0xd800;
        FP_OFF(fpScRegs) = 0;

enable_bus();           /* read m mode psotition */
        bTemp = *fpScRegs;
        bTemp = *fpScRegs+1;
        bTemp = *fpScRegs;
        bTemp = *fpScRegs+1;
#endif
/*------------------------------------------------------------------*/
```

```
    /** Scan multi-probe ID and update (1 port per loop)  **/
    if (bMPScan) {
       MPScan(nPort++) ;
       nPort %= 4 ;
    }

/* If the transducer has changed, update */
#ifdef MAINTENANCE
    if (!No_Xdcr_Change)
#endif
                                            /* #DOP */
    if (New_Second) {
       New_Second = FALSE;
       if (nVersionCount < 3) {
          nVersionCount++ ;
       } else {
          if (bVersionOn) {
             bVersionOn = FALSE ;
             close_window() ;
          }
       }

/** If not scanning multi-probe AND not in doppler-pencil  **/
       /** then detect changes as normal                          **/
       if ( !bMPScan && !(DopCtrl.bDoppler && DopCtrl.bPencilSlctd) ) {
          if (xdcr_change_bus_on()) {
             DopplerArrayChange();
             (void) change_xdcr( xdcr_num());
          }
       }
    } else {
       if ( !bMPScan && !(DopCtrl.bDoppler && DopCtrl.bPencilSlctd) ) {
          if (xdcr_change()) {
             DopplerArrayChange();
             (void) change_xdcr( xdcr_num());
          }
       }
    }
                                            /* #DOP */
#ifdef MAINTENANCE
    else {
       if (xdcr_change())   /* xdcr_change() will turn off tx pulsing
                               when the EID is attached. */
          set_tx_power();   /* turns high voltage back on it there is now
                               a valid xdcr attached. */
    }
endif /* Keep the date and time */ update_date_and_time();

ifdef MAINTENANCE
    update_beamplot_display();
endif if (!bMPScan) {
       reset_watchdog(RWT_LONG);     /* #DOP 10 second timeout  */
    }

*------------------------------------------------------------------------
      Test errors detected in timer tick  (..\cbb\cbbasm.asm)
--------------------------------------------------------------------*/ if ( (nMModeSpeedError) && (M_Mode_On) ) {   /* set in timer tick */
         m_mode_speed_error();                    /* bk chg. 11.22.89 */
    } if (nPrfError)                               /* set in timer tick */
       prf_error();                              /* bk chg 11.22.89 */ doppler_main_loop();         /* #DOP Execute doppler main loop  */
```

What is claimed is:

1. An ultrasonic imager comprising:
    a plurality of ports each capable of being connected to an ultrasonic transducer having a plurality of attributes;
    a control unit for polling each port to determine attributes of the transducer connected to each port; and
    a display for displaying the transducer attributes determined from the polling of the ports.

2. The imager of claim 1 wherein the plurality of attributes include the emitted frequency of the transducer and the display displays the emitted frequency.

3. The imager of claim 1 wherein the plurality of attributes include the transducer array configuration and the display displays the transducer array configuration.

4. The imager of claim 1 wherein the control unit also polls each port to determine whether a transducer is connected to each port and wherein the display displays whether a transducer is connected at each port.

5. The imager of claim 1 wherein the control unit drives transducers connected to the ports and wherein the control unit comprises a selector for determining which transducer is to be driven.

6. The imager of claim 5 wherein the selector comprises a trackball for selecting a transducer, the trackball being in communication with an indicator on the display so that, through rolling the trackball, a transducer is selected by positioning the indicator proximate a displayed set of attributes corresponding to the selected transducer.

7. The imager of claim 5 wherein the selector comprises a keyboard for selecting a transducer, the keyboard being in communication with an indicator on the display so that, through keystrokes, a transducer is selected by positioning the indicator proximate a displayed set of attributes corresponding to the selected transducer.

8. An ultrasonic imager comprising:
    a plurality of ultrasonic transducers for transmitting and receiving ultrasonic signals and converting the received ultrasonic signals to electrical signals, each transducer being individually operable and having a set of attributes; and
    a control unit coupled to the transducers for individually operating the transducers, the control unit comprising:
    a display for simultaneously displaying at least some of the set of attributes of each transducer and
    a selector for determining which transducer is to be operated.

9. The imager of claim 8 wherein the set of attributes includes the transducer's transmitted frequency and the display displays the transducer's transmitted frequency.

10. The imager of claim 8 wherein the set of attributes includes the transducer array configuration and the display displays the transducer array configuration.

11. The imager of claim 8 wherein the display indicates which, if any, of the transducers are being driven.

12. The imager of claim 8 wherein the selector comprises a trackball for selecting a transducer, the trackball being coupled to an indicator on the display so that, through rolling the trackball, a transducer is selected by positioning the indicator proximate a displayed set of attributes corresponding to the selected transducer.

13. The imager of claim 8 wherein the selector comprises a keyboard for selecting a transducer, the keyboard being in communication with an indicator on the display so that, through keystrokes, a transducer is selected by positioning the indicator proximate a displayed set of attributes corresponding to the selected transducer.

14. The imager of claim 8 wherein the transducers are replaceable and the display is changeable upon replacing a transducer.

15. The imager of claim 14 wherein the control unit polls the transducers to determine the displayed attributes and the control unit adjusts the display of attributes in response to the poll.

16. A method for driving an ultrasonic imager capable of supporting a plurality of replaceable ultrasonic transducers, each transducer being connectable to the imager through at least one of a plurality of imager ports, each transducer having a plurality of attributes, the method comprising:
    determining the attributes of transducers connected to the imager ports;
    displaying the attributes of transducers for which the attributes have been determined;
    selecting a transducer connected to one of the plurality of ports for use;
    displaying an indication of which transducer has been selected; and
    driving the selected transducer.

17. The method of claim 16 wherein determining the attributes comprises:
    determining the identity of transducers, connected to the imager ports; and
    consulting a memory of transducer attributes to obtain the attributes of each identified transducer using the transducer's identity.

18. The method of claim 16 wherein determining the attributes comprises:
    obtaining an identification number from transducers connected to the imager ports; and
    consulting a memory of transducer attributes to obtain the attributes of transducers corresponding to the identification numbers.

19. The method of claim 16 wherein displaying the attributes comprises displaying the attributes of each transducer in association with an indication of the port to which it is connected.

20. The method of claim 16 comprising:
    determining whether a transducer has been connected to each one of the plurality of ports; and
    for each port to which no transducer is connected, displaying that no transducer has been connected to the respective port.

21. The method of claim 16 wherein selecting a transducer comprises entering a command through a keyboard.

22. The method of claim 16 comprising displaying an indication in association with a transducer and wherein selecting a transducer comprises entering a command through a keyboard to associate the indication with the transducer to be selected.

23. The method of claim 22 wherein entering a command comprises striking a cursor key.

24. The method of claim 22 wherein entering a command comprises rolling a trackball.

25. The method of claim 16 wherein each transducer is drivable according to adjustable operating parameters and wherein driving the selected transducer comprises:
    determining the adjustable operating parameters for the selected transducer;
displaying the adjustable operating parameters;
adjusting the operating parameters through entering commands on a keyboard;
displaying the entered adjustments; and
driving the selected transducer according to the entered adjustments.

26. An ultrasound imaging system comprising:
a plurality of ultrasound transducers;
electronic circuitry for exciting one of the transducers to emit ultrasonic pulses and for processing ultrasonic echoes received by the one transducer to produce electrical image control signals;
means for selectively connecting one of the transducers to the electronic circuitry to operate the selected transducer;
means for displaying ultrasonic images on a screen responsive to the image control signals; and
means for displaying on the screen a visual representation of the selected transducer.

27. The imaging system of claim 26, in which the means for selectively connecting comprises:
a plurality of ports;
means for selectively connecting one of the ports to the electronic circuitry;
a plurality of connector blocks equal in number to the transducers removably mated with respective ports; and
a plurality of cables equal in number to the transducers connecting the transducers to the respective blocks.

28. The imaging system of claim 27, in which the number of ports is greater than the number of transducers.

29. The imaging system of claim 26, in which the means for displaying a visual representation of the selected transducer comprises:
means for displaying on the screen visual representations of the plurality of transducers; and
means for designating on the screen the visual representation of the selected transducer.

30. The imaging system of claim 29, in which the visual representations are boxes.

31. The imaging system of claim 30, in which the designating means comprises means for highlighting the box representing the selected transducer.

32. The imaging system of claim 28, in which the means for displaying a visual representation of the selected transducer comprises:
means for displaying on the screen visual representations of the plurality of ports; and
means for designating on the screen a visual representation of the selected port;
the system additionally comprising means for designating on the screen a visual representation of those ports that are mated with the blocks.

33. The imaging system of claim 29, additionally comprising means for displaying on the screen in connection with the visual representation of each transducer a visual representation of at least one attribute of such transducer.

34. The imaging system of claim 27, additionally comprising:
means for uniquely identifying each transducer;
means for displaying on the screen visual representations of the plurality of ports; and
means responsive to the identifying means for displaying on the screen in proximity to each visual representation of a port an identification of the transducer connected to such port.

35. The imaging system of claim 34, in which the means for displaying an identification comprises means for displaying one or more attributes of the transducer.

36. The imaging system of claim 35, in which the identifying means comprises means for generating a unique identifying signal in each transducer and means for transmitting the identifying signal to the port mated with the transducer.

37. The imaging system of claim 36, in which the means for displaying one or more attributes comprises means for sensing the identifying signals, means for storing the attributes of the transducers in memory, and means responsive to the sensing means for retrieving from memory and displaying the attributes of the identified transducers.

38. The imaging system of claim 37, in which the visual representations of the plurality of ports are boxes and the means responsive to the sensing means displays the attributes of the transducers connected to the respective ports in the corresponding boxes.

39. The imaging system of claim 38, in which the visual representation of the selected transducer comprises a highlighted box.

* * * * *